（12） United States Patent
Takahashi et al.

(10) Patent No.: US 10,034,885 B2
(45) Date of Patent: Jul. 31, 2018

(54) CORNEAL THICKNESS MODULATING AGENT

(71) Applicant: KOWA COMPANY, LTD., Nagoya-shi, Aichi (JP)

(72) Inventors: Hiroyuki Takahashi, Tokyo (JP); Kiyoshi Toya, Tokyo (JP); Akifumi Tsuchiura, Tokyo (JP)

(73) Assignee: KOWA COMPANY, LTD., Nagoya-shi (JP)

( * ) Notice: Subject to any disclaimer, the term of this patent is extended or adjusted under 35 U.S.C. 154(b) by 0 days.

(21) Appl. No.: 15/511,736

(22) PCT Filed: Sep. 24, 2015

(86) PCT No.: PCT/JP2015/076835
§ 371 (c)(1),
(2) Date: Mar. 16, 2017

(87) PCT Pub. No.: WO2016/047647
PCT Pub. Date: Mar. 31, 2016

(65) Prior Publication Data
US 2017/0290840 A1    Oct. 12, 2017

(30) Foreign Application Priority Data

Sep. 24, 2014    (JP) ................. 2014-193363

(51) Int. Cl.
*A61K 31/551*    (2006.01)
*C07D 401/12*    (2006.01)
*A61K 9/00*    (2006.01)

(52) U.S. Cl.
CPC .......... *A61K 31/551* (2013.01); *A61K 9/0048* (2013.01)

(58) Field of Classification Search
CPC ............................ A61K 31/551; C07D 401/12
USPC .......................................... 514/218; 540/575
See application file for complete search history.

(56) References Cited

U.S. PATENT DOCUMENTS

| 8,193,193 | B2 | 6/2012 | Mizuno et al. |
| 2010/0209402 | A1 | 8/2010 | Koizumi et al. |
| 2012/0288482 | A1 | 11/2012 | Takahashi et al. |
| 2014/0378441 | A1 | 12/2014 | Ishibashi et al. |

FOREIGN PATENT DOCUMENTS

| EP | 1 905 452 A1 | 4/2008 |
| EP | 2 193 806 A1 | 6/2010 |
| JP | 11-349482 A | 12/1999 |
| JP | 2013-515676 A | 5/2013 |
| JP | 5557408 B1 | 7/2014 |
| WO | 1999/064011 A1 | 12/1999 |
| WO | 2007/007737 A1 | 1/2007 |
| WO | 2009/028631 A1 | 3/2009 |
| WO | 2011/080984 A1 | 7/2011 |
| WO | 2011/081221 A1 | 7/2011 |

OTHER PUBLICATIONS

International Search Report dated Dec. 22, 2015, issued in counterpart application No. PCT/JP2015/076835 (3 pages).
Sakamoto et al., "Ferret animal model of corneal endothelial dysfunction for evaluation of drug effect on corneal endothelial wound healing", Animal's Eye Research, 2013, vol. 32, pp. 15-21, cited in ISR. (7 pages).
Vassilev et al., "Loss of N-Cadherin from the Endothelium Causes Stromal Edema and Epithelial Dysgenesis in the Mouse Cornea", Investigative Ophthalmology & Visual Science, 2012, vol. 53, No. 11, pp. 7183-7193,cited in ISR. (11 pages).
Miyoshi et al., "Structural and functional associations of apical junctions with cytoskeleton", Biochimica et Biophysica Acta, 2008, vol. 1778(3), pp. 670-691, cited in ISR. (22 pages).
Wecker et al., "Effects of TGF-ß2 on Cadherins and ß-Catenin in Human Trabecular Meshwork Cells", Investigative Ophthalmology & Visual Science, 2013, vol. 54, No. 10, pp. 6456-6462, cited in ISR. (7 pages).
Koizumi, "Development of new therapeutic modalities for corneal endothelial disease using somatic stem cells", vol. 241, No. 10, Jul. 9, 2012, pp. 765-770, (6 pages).
Bi et al., "Regulation of functional corneal endothelial cells isolated from sphere colonies by Rho-associated protein kinase inhibitor", Experimental and Therapeutic Medicine, 2013, 5, pp. 433-437, (5 pages).
Lee et al., "FGF-2 induced reorganization and disruption of actin cytoskeleton through PI 3-kinase, Rho, and Cdc42 in corneal endothelial cells", Molecular Vision, 2003, 9, pp. 624-634, (11 pages).
Lee et al., "FGF-2-Induced Wound Healing in Corneal Endothelial Cells Requires Cdc42 Activation and Rho Inactivation through the Phosphatidylinositol 3-Kinase Pathway", Investigative Ophthalmology & Visual Science, Apr. 2006, vol. 47, No. 4, pp. 1376-1386, (11 pages).
Okumura et al., "Enhancement of corneal endothelium wound healing by Rho-associated kinase (ROCK) inhibitor eye drops", Br. J. Ophthalmol., 2011, 95, pp. 1006-1009, (4 pages).
Koizumi et al., "Rho-Associated Kinase Inhibitor Eye Drop Treatment as a Possible Medical Treatment for Fuchs Corneal Dystrophy", Cornea, Aug. 2013, vol. 32, No. 8, pp. 1167-1170, (4 pages).
Okumura et al., "Involvement of Cyclin D and p27 in Cell Proliferation Mediated by ROCK Inhibitors Y-27632 and Y-39983 During Corneal Endothelium Wound Healing", IOVS, 2014, vol. 55, No. 1, pp. 318-329, (12 pages).
Notification of Transmittal of Translation of the International Preliminary Report on Patentability (Form PCT/IB/338) issued mailed in counterpart International Application No. PCT/JP2015/076835 dated Apr. 6, 2017, with Forms PCT/IB/373 and PCT/ISA/237. (15 pages)
Koizumi, N., "Regeneration Medicine for Ophthalmic Diseases Development of New Therapeutic Modalities for Corneal Endothelial Disease Using Somatic Stem Cells"; vol. 241, No. 10, Jul. 9, 2012, partial English translation. (3 pages).

(Continued)

*Primary Examiner* — Brenda L Coleman
(74) *Attorney, Agent, or Firm* — Westerman, Hattori, Daniels & Adrian, LLP

(57) ABSTRACT

The present invention provides a novel corneal thickness modulating agent. The present invention pertains to a corneal thickness modulating agent containing 1-(4-fluoro-5-isoquinolinesulfonyl)-2-methyl-1,4-homopiperazine or a salt thereof or a solvate thereof.

10 Claims, 1 Drawing Sheet

(56) References Cited

OTHER PUBLICATIONS

Isobe et al.,"Effects of K-115, a Rho-Kinase Inhibitor, on Aqueous Humor Dynamics in Rabbits", Current Eye Research, Informa Healthcare USA, US, Aug. 2014, pp. 813-822, vol. 39, No. 8. (10 pages).(cited in Extended (Supplementary) European Search Report dated May 22, 2018).

Nakagawa et al.,"Morphological Changes of Human Corneal Endothelial Cells after Rho-Associated Kinase inhibitor Eye Drop (Ripasudil) Administration: A Prospective Open-Label Clinical Study", PLOS ONE, Sep. 2015, p. e0136802, vol. 10, No. 9. (15 pages).(cited in Extended (Supplementary) European Search Report dated May 22, 2018).

Wato et al.,"Safety evaluation of morphological changes in corneal endothelial cells induced by K-115 in cynomolgus monkeys", Fundamental Toxicological Sciences, Dec. 2014. pp. 39-47, vol. 1, No. 2. (9 pages).(cited in Extended (Supplementary) European Search Report dated May 22, 2018).

Extended (Supplementary) European Search Report dated May 22, 2018, issued in counterpart application No. 15844777.1. (10 pages).

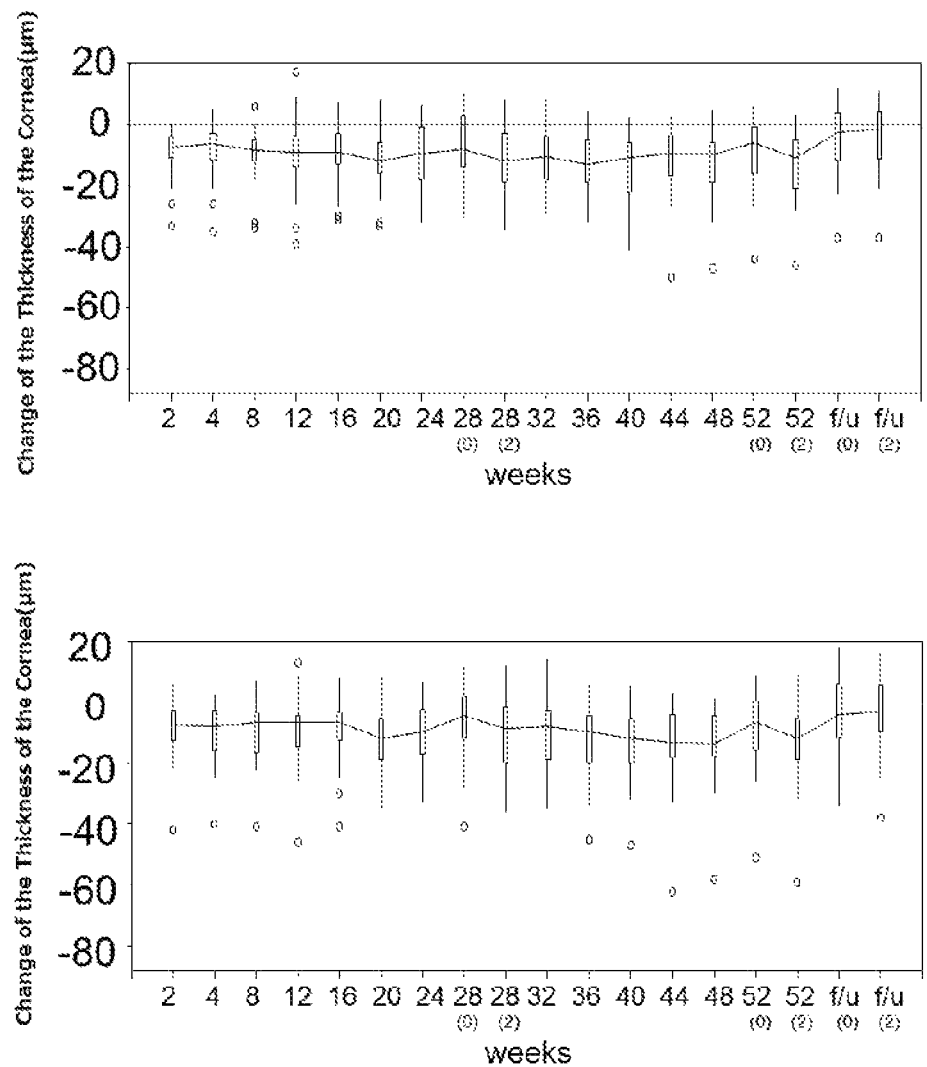

CORNEAL THICKNESS MODULATING AGENT

TECHNICAL FIELD

The present invention relates to an agent for modulating corneal thickness. More specifically, the present invention relates to an agent for modulating corneal thickness containing, as an active ingredient, 1-(4-fluoro-5-isoquinolinesulfonyl)-2-methyl-1,4-homopiperazine or a salt thereof, or a solvate thereof.

BACKGROUND ART

The cornea is an important tissue not only composing the wall of the eyeball with the sclera, but also behaving as an entrance to take in an image of the outside into the eye by virtue of a transparent tissue. Unlike other biotissues, the cornea has no blood vessel and is transparent, and both of the surfaces are smooth and spherical. The outer surface of the cornea is covered with the tear film, and the inner surface thereof contacts with the anterior chamber that is filled with aqueous humor.

The cornea has a thickness of approximately 500 μm at the central part, and consists of five layers of, starting from the outside, corneal epithelium, Bowman membrane, stroma, Descemet membrane, and corneal endothelium. The corneal epithelial layer has a thickness of approximately 10% of the whole thickness of the cornea, and is formed of corneal epithelial cells. When the corneal epithelium is injured, peripheral epithelial cells migrate to the injured part and proliferate there to repair damage. The thickness of the corneal stroma accounts for approximately 90% of the whole thickness of the cornea. The main component of the corneal stroma is collagen, and besides, the corneal stroma contains mucopolysaccharide. The mucopolysaccharide is water absorptive, and tends to bulging (swelling) by absorbing water. However, the water content in the corneal stroma is maintained constant due to the pumping function and barrier function of the corneal endothelium.

The corneal endothelium is composed of corneal endothelial cells. The corneal endothelium cannot regenerate once it falls away because human corneal endothelial cells do not proliferate. When human corneal endothelial cells are injured and then fall away, the defect cannot be repaired by the cell proliferation. Alternatively, peripheral endothelial cells will migrate to and enlarge in the defect area and then form new cell adhesion, thereby compensating the defect. Therefore, the adhesive property of a human corneal endothelial cell is an important function of repairing the injured part. In addition, since the number of corneal endothelial cells is limited, when the corneal endothelium is suffered serious injury the corneal endothelium cells cannot repair it and thus the defect remains in the corneal endothelium. The defect formed in the corneal endothelium leads to irreversible serious dysfunction. Specifically, when the density of corneal endothelial cells is approximately 500 cells/$mm^2$ or less, it is impossible to repair the defect in the corneal endothelium, causing corneal edema (bullous keratopathy) associated with irreversible opacity. Note that it is considered that the density of normal corneal endothelial cells is approximately 2500 to 3000 cells/$mm^2$.

A corneal endothelial cell has the pumping function of draining water from the corneal stroma which tends to swelling by absorbing the water into the anterior chamber, and the barrier function of controlling transfer of the water from the anterior chamber to the corneal stroma. When these functions of corneal endothelial cells decrease, the corneal stroma will contain excessive water, thereby not only increasing the thickness of the cornea, but also causing edema (bullous keratopathy) associated with irreversible opacity, with the result that the visual acuity will extremely decrease. Because swelling of the cornea increases the thickness of the cornea and leads to occurrence of edema, it is necessary to thin the cornea and to prevent the cornea from swelling.

The dysfunction of the corneal endothelium is considered to account for approximately 60% of the whole dysfunction of the cornea. The defect in the corneal endothelium due to physical injury, progressive corneal endothelial dystrophy (typically Fuchs corneal dystrophy) or the like results in bullous keratopathy associated with irreversible corneal edema. When the visual acuity extremely decreases, corneal transplant is required.

Although human corneal endothelial cells do not proliferate in vivo, it has been examined to culture them in vitro (see Non-Patent Documents 1 and 2). This is because it is possible to treat the cornea by transplanting human corneal endothelial cells which have been cultured and proliferated in vitro.

Thus, development is desired of not only a medical agent for enhancing the adhesive property of a corneal endothelial cell, and furthermore for repairing the injured part of the corneal endothelium or for maintaining and recovering the functions of the corneal endothelium, but also a culture medium for culturing and proliferating a human corneal endothelial cell, a preservation solution for storing a corneal endothelial cell or a corneal endothelial tissue until transplant, a medical agent for modulating the thickness of the cornea, and the like.

Rho kinase (Rho-associated, coiled-coil containing protein kinase: ROCK) is a serine threonine kinase having a molecular weight of approximately 160 kDa, and its gene is highly conserved from lower animals such as nematode and drosophila to humans. Rho kinase contributes to physiological functions such as contraction of smooth-muscle cells, control of cell morphology, migration, and control of gene expression. Development is promoted of Rho kinase inhibitor as a therapeutic agent for circulatory disease and the like.

In addition, in recent years, development thereof has been made as a medicine for topical administration for use in treatment of eye diseases such as glaucoma. Furthermore, as to culture of a corneal endothelial cell, it has been reported that a rabbit corneal endothelial cell can be cultured in the presence of (+)-trans-4-(1-aminoethyl)-1-(4-pyridylaminocarbonyl)cyclohexane (hereinafter referred to as Y-27632) that is one kind of Rho kinase inhibitor (see Non-Patent Documents 3 and 4), and it has been reported that a monkey corneal endothelial cell can also be cultured in the same way (see Patent Document 1). Patent Document 1 reports that the adhesive property of a rabbit corneal endothelial cell is enhanced also with 1-(5-isoquinolinesulfonyl)-1,4-homopiperazine) hereinafter referred to as fasudil). Moreover, treatment of injured rabbit corneal endothelium with Y-27632 (see Non-Patent Document 5) and treatment of human Fuchs corneal dystrophy with Y-27632 (see Non-Patent. Document 6) have been reported. In addition, treatment of injured rabbit corneal endothelium with (R)—(+)—N-(1H-pyrrolo[2,3-b]pyridin-4-yl)-4-(1-aminoethyl) benzamide (hereinafter, referred to as Y-39383) also has been reported (see Patent Document 2 and Non-Patent Document 7). According to Non-Patent Document 7, the 50% inhibitory concentrations ($IC_{50}$) of Y-33983 and Y-27632 for Rho kinase are 0.0036 μM and 0.11 μM, respectively, between which there is an approximately 30 times difference. The difference is considered to result in a difference of activity for a corneal endothelial cell.

Both Y-27632 and Y-39983 used in these Documents are N-pyridyl amide compounds, whereas fasudil is a 1-sulfone-1,4-homopiperazine compound.

On the other hand, it has been disclosed that 1-(4-fluoro-5-isoquinolinesulfonyl)-2-methyl-1,4-homopiperazine (hereinafter, also referred to as Compound A) is a 1-sulfone-1,4-homopiperazine compound like fasudil, but has a higher selectivity than that of fasudil, and has a higher Rho kinase inhibitory activity than that of fasudil, and it has been reported that the compound is useful for prevention or treatment of asthma (see Compound 6 in Patent Document 3). Patent Document 3 discloses that the 50% inhibitory concentrations ($IC_{50}$) of Compound A and fasudil for Rho kinase are 0.2 μM and 1.5 μM, respectively. In comparison with the disclosure in above-mentioned Non-Patent Document 7, the 50% inhibitory concentration ($IC_{50}$) of Compound A for Rho kinase is considered to be more potent than that of fasudil, but less potent than or similar to that of Y-27632.

As to use of Compound A for eye diseases, it has been reported that combination of Compound A with carbonic anhydrase inhibitor is useful for prevention or treatment of glaucoma (see Patent Document 4), and Compound A is useful for prevention or treatment of ocular fundus disease (see Patent Document 5), but the effect of Compound A on the corneal thickness has not been reported.

CITATION LIST

Patent Document

Patent Document 1: WO 2009/028631 A1
Patent Document 2: JP 2013-515676 A
Patent Document 3: JP H11-349482 A
Patent Document 4: WO 2007/007737 A1
Patent Document 5: JP 5557408 B1

Non-Patent Document

Non-Patent Document 1: Koizumi N., Journal of Clinical and Experimental Medicine, 2012, 241(10), 765-770
Non-Patent Document 2: Bi Y-L. et al., Experimental and Therapeutic Medicine, 2013, 5, 433-437
Non-Patent Document 3: Lee H. T. et al., Molecular Vision, 2003, 9, 624-634
Non-Patent Document 4: Lee J. G. et al., IOVS, 2006, 47(4), 1376-1386
Non-Patent Document 5: Okurmura N. et al., Br. J. Ophthalmol., 2011, 95, 1006-1009
Non-Patent Document 6: Koizumi N. et al., Cornea, 2013, 32(8), 1167-1170
Non-Patent Document 7: Okurmura N. et al., IOVS, 2014, 55(1), 318-329

SUMMARY OF THE INVENTION

Problems to be Solved by the Invention

The present invention provides an agent for modulating corneal thickness to maintain and recover the corneal thickness, and a method for maintaining and recovering the corneal thickness using the same, e.g., a method for thinning a corneal.

Means for Solving the Problems

As a result of intensive studies carried out by the inventors in order to solve the above-mentioned problems, it is found that 1-(4-fluoro-5-isoquinolinesulfonyl)-2-methyl-1,4-homopiperazine (hereinafter also referred to as Compound A) or a salt thereof or a solvate thereof is capable of thinning the thickness of the cornea and maintaining the thinness, and results in a medical agent for the corneal tissue which is safer and excellent in effectiveness. In addition, it is found that it is also possible to instill the substance in the eye, enabling its formulation which imposes only a slight burden on a patient.

In other words, the present invention relates to an agent for modulating corneal thickness comprising 1-(4-fluoro-5-isoquinolinesulfonyl)-2-methyl-1,4-homopiperazine or a salt thereof, or a solvate thereof.

In addition, the present invention relates to an agent for thinning the cornea comprising 1-(4-fluoro-5-isoquinolinesulfonyl)-2-methyl-1,4-homopiperazine or a salt thereof, or a solvate thereof.

Furthermore, the present invention relates to an agent for preventing corneal edema comprising 1-(4-fluoro-5-isoquinolinesulfonyl)-2-methyl-1,4-homopiperazine or a salt thereof, or a solvate thereof.

A more detailed description of the present invention is as follows.

(1) An agent for modulating corneal thickness comprising 1-(4-fluoro-5-isoquinolinesulfonyl)-2-methyl-1,4-homopiperazine or a salt thereof, or a solvate thereof.

(2) The agent for modulating corneal thickness of above-mentioned (1), wherein the 1-(4-fluoro-5-isoquinolinesulfonyl)-2-methyl-1,4-homopiperazine is (S)-(−)-1-(4-fluoro-5-isoquinolinesulfonyl)-2-methyl-1,4-homopiperazine (hereinafter also referred to as Compound B).

(3) The agent for modulating corneal thickness of above-mentioned (1) or (2), wherein the agent for modulating corneal thickness is an agent for thinning a cornea.

(4) The agent for modulating corneal thickness of above-mentioned (1) or (2), wherein the agent for modulating corneal thickness is an agent for preventing and/or treating corneal edema.

(5) The agent for modulating corneal thickness of above-mentioned (1) or (2), wherein the agent for modulating corneal thickness is an agent for preventing and/or treating disorder of corneal endothelium.

(6) The agent for modulating corneal thickness of above-mentioned (5), wherein the disorder of corneal endothelium is a disease of corneal endothelium such as bullous keratopathy or corneal endotheliitis.

(7) The agent for modulating corneal thickness of any one of above-mentioned (1) to (6), wherein the agent for modulating corneal thickness is a liquid formulation.

(8) The agent for modulating corneal thickness of any one of above-mentioned (1) to (7), wherein the agent for modulating corneal thickness is an eyedrop.

(9) The agent for modulating corneal thickness of any one of above-mentioned (1) to (8), wherein the cornea is a primate cornea.

(10) The agent for modulating corneal thickness of any one of above-mentioned (1) to (9), wherein the cornea is a human cornea.

(11) A method for producing a formulation of the agent for modulating corneal thickness of any one of above-mentioned (1) to (10), comprising: mixing 1-(4-fluoro-5- isoquinolinesulfonyl)-2-methyl-1,4-homopiperazine or a salt thereof, or a solvate thereof with a pharmaceutically acceptable carrier.

Effects of the Invention

The present invention provides an agent for modulating cornea thickness in order to prevent and/or treat corneal disorder causing by the abnormality of the corneal thickness. The agent for modulating corneal thickness of the present invention may prevent and/or treat various kinds of disorders of the corneal endothelium, for example, a disease of the corneal endothelium such as bullous keratopathy or corneal endotheliitis, or the abnormalities of the corneal endothelium, caused by corneal transplant or the like. Moreover, the agent for modulating corneal thickness of the present invention is effective in thinning the cornea and maintaining the thinness even though the active ingredient thereof is at low concentrations, therefore the agent for modulating corneal thickness of the present invention may be used as a pharmaceutical composition which is highly effective and safe with few side effects.

In addition, the agent for modulating corneal thickness of the present invention may provide an eyedrop imposing only a slight burden on a patient.

BRIEF DESCRIPTION OF DRAWINGS

The figure illustrates change of the thickness of the cornea when Compound B was instilled in the eye of humans in a box-and-whisker plot format.

MODES FOR CARRYING OUT THE INVENTION

Hereinafter, a description is made of the present invention in more detail.

Compound A in the present invention has one asymmetric carbon atom, leading to an (R) isomer and (S) isomer. In the present invention, any of the (R) isomer, (S) isomer, and a mixture thereof may be used. As the pharmaceutical active ingredient, a highly-pure optically-active material of the (R) isomer or (S) isomer is preferable. From the terms of the desired activity, the (S) isomer is the more preferable than the (R) isomer. In this description, the (S) isomer is simply represented as Compound B.

1-(4-Fluoro-5-isoquinolinesulfonyl)-2-methyl-1,4-homopiperazine, which is an active ingredient of the present invention, is publicly known as a therapeutic agent for cerebrovascular or therapeutic agent for asthma, or a compound having a substance P antagonistic effect, leukotriene $D_4$ antagonistic effect and Rho kinase inhibitory effect (see Patent Document 3), which may be produced by a publicly known method, e.g., the method disclosed in WO 99/20620 A1.

A salt of Compound A includes, for example, a salt formed with an inorganic acid such as hydrochloric acid, sulfuric acid, nitric acid, hydrofluoric acid or hydrobromic acid, or a salt formed with organic acid such as acetic acid, tartaric acid, lactic acid, citric acid, fumaric acid, maleic acid, succinic acid, methanesulfonic acid, ethanesulfonic acid, benzenesulphonic acid, toluenesulfonic acid, naphthalenesulfonic acid or camphorsulfonic acid. In particular, a hydrochloride salt is preferable.

Compound A or a salt thereof may exist not only as an unsolvated type but also as a hydrate or solvate. Although a hydrate is preferable, the present invention includes all crystal forms and hydrates or solvates.

In the present invention, an "agent for modulating corneal thickness" refers to those for modulating the thickness of the cornea to maintain the function of the normal cornea. Since the thickness of the cornea mainly depends on the function of the corneal endothelium, the "agent for modulating corneal thickness" of the present invention is considered to be capable of modulating the thickness of the cornea when the corneal endothelium has dysfunction such as an accelerated or reduced function of the corneal endothelium, by regulating the concerned function to bring about a more normal state. In other words, since the corneal endothelium has the pumping function, barrier function or the like which is important in maintaining the visual acuity, it is considered that when these functions are accelerated, the agent of the present invention suppresses them, whereas when these functions are reduced, the agent enhances them, in order to make the corneal thickness more normal.

Because administering the "agent for modulating corneal thickness" of the present invention makes it possible to modulate the function of the corneal endothelium, thereby thinning the thickness of the cornea (thinning), the "agent for modulating corneal thickness" of the present invention may also be used as an agent for thinning the cornea, an agent for preventing or treating corneal edema, and/or an agent for preventing or treating disorder of the corneal endothelium.

The "agent for modulating corneal thickness" of the present invention is formulated into a dosage form suitable for topical administration to the eye using a usual formulation technology frequently used in the art. As the dosage form, for example, a liquid formulation such as, but is not limited to, an injection for anterior chamber, ocular perfusion, or eyedrop is preferable. As the preferable formulation, from the terms of the therapeutic effect, an injection for anterior chamber or ocular perfusion is a preferable dosage form, but imposes a significant burden on a patient. Accordingly, from the terms of easy administration, the preferable formulation includes an eyedrop.

The eyedrop of the present invention contains Compound A, preferably Compound B or a salt thereof or a solvate thereof, as an active ingredient, and an acceptable carrier for the eyedrop.

Preparation of the eyedrop may be achieved by, for example, dissolving or suspending the desired above-mentioned component in an aqueous solvent such as sterilized pure water or saline, or a nonaqueous solvent such as vegetable oil including cottonseed oil, soy oil, sesame oil or peanut oil, adjusting the solution or suspension pressure to a predetermined osmotic pressure, and performing sterilization treatment such as filtration sterilization. Note that when preparing an ophthalmic ointment, an ointment base may be contained in addition to the above-mentioned various components. The said ointment base preferably includes, but not particularly limited to; an oleaginous base such as vaseline, liquid paraffin or polyethylene; an emulsion base in which the oil phase and aqueous phase are emulsified with a surfactant or the like; a water-soluble base consisting of hydroxypropylmethylcellulose, carboxymethylcellulose, polyethyleneglycol, or the like.

When using Compound A, preferably Compound B or a salt thereof, or a solvate thereof for the "agent for modulating corneal thickness" of the present invention, the dose depends on the body weight, age, sex, symptom of a patient, the dosage form, the number of doses and the like, but generally, the dose of Compound A, preferably Compound B for an adult includes a range of 0.025-10000 μg a day, preferably 0.025-2000 μg, more preferably 0.1-2000 μg, further 0.025-200 μg, 0.025-100 μg.

When using the same as an eyedrop, the concentration of the active ingredient may be approximately 0.0001-5 w/v %, preferably approximately 0.01-4 w/v %.

In addition, the number of doses is not limited in particular, but the administration is preferably performed one or several times, and in case of the liquid eyedrop, one to several drops may be instilled in the eye for once administration.

A subject to which the "agent for modulating corneal thickness" of the present invention is to be administrated includes mammals (e.g., human, mouse, rat, hamster, rabbit, cat, dog, cow, horse, sheep, or monkey). The mammals preferably include primates such as human or monkey, particularly preferably include human.

EXAMPLES

Example 1

Change of thickness of cornea in human:

In a long-term administration test of Compound B in a subject having ophthalmologic disease, the influence on the cornea was examined (27-34 examples). In other words, in an group administered an eyedrop consisting of 0.4% Compound B twice a day for 52 weeks, the corneal thickness was measured using pachymeter before starting administration (week 0), 2 weeks after starting administration, 4 weeks after starting administration, and every 4 weeks thereafter. Measurement was performed five times, and the mean value calculated from the five measurements was adopted. In the measuring day, the drop was instilled in the eye at 9:00 and measurement was performed at 11:00. Note that at week 28, week 52, and during the follow-up (7-28 days after the last administration day), measurement was performed twice at 9:00 (at week 28 and week 52, it was done before the instillation) and 11:00.

The result is shown in FIG. 1. The upper part in FIG. 1 represents the result from the right eye, and the lower part in FIG. 1 represents the result from the left eye. The vertical axis represents changing values (μm) from week 0, and the horizontal axis represents the week for administration. At week 28, week 52, and during the follow-up (f/u), the measurement at 9:00 is represented with (0) and the measurement at 11:00 is represented with (2). Note that the corneal thickness before administration (week 0) was 531.6±28.0 μm for the right eye, and 530.9±27.9 μm for the left eye (both representing the mean value±standard deviation).

It was found that the thickness of the cornea decreased during the period for administration of Compound B of the present invention. The thickness of the cornea was held at a nearly constant value during the continued administration. In addition, at week 28 and week 52, the thickness of the cornea before instillation (0) had a tendency to return to the value before starting administration of Compound B (week 0), but the thickness of the cornea decreased 2 hours after instillation (2).

The invention claimed is:

1. A method of modulating a thickness of a cornea of a subject, the method comprising:
   measuring the thickness of the cornea of the subject, and administrating 1-(4-fluoro-5-isoquinolinesulfonyl)-2-methyl-1,4-homopiperazine or a salt thereof, or a solvate thereof to the subject.

2. The method according to claim 1, wherein said 1-(4-fluoro-5-isoquinolinesulfonyl)-2-methyl-1,4-homopiperazine is (S)-(-)-1-(4-fluoro-5-isoquinolinesulfonyl)-2-methyl-1,4-homopiperazine.

3. The method according to claim 1, wherein said administration is effective in reducing the thickness of the cornea.

4. The method according to claim 1, wherein said 1-(4-fluoro-5-isoquinolinesulfonyl)-2-methyl-1,4-homopiperazine is administered in an effective amount to treat corneal edema.

5. The method according to claim 1, wherein a liquid formulation containing said 1-(4-fluoro-5-isoquinolinesulfonyl)-2-methyl-1,4-homopiperazine is administered.

6. The method according to claim 1, wherein the cornea is a primate cornea.

7. The method according to claim 1, wherein said 1-(4-fluoro-5-isoquinolinesulfonyl)-2-methyl-1,4-homopiperazine is administered at a dose of 0.025 to 10,000 μg/day.

8. The method according to claim 1, wherein said 1-(4-fluoro-5-isoquinolinesulfonyl)-2-methyl-1,4-homopiperazine is administered to an eye of the subject.

9. The method according to claim 8, wherein an eyedrop containing 0.0001 to 5 w/v % of said 1-(4-fluoro-5-isoquinolinesulfonyl)-2-methyl-1,4-homopiperazine is administered.

10. The method according to claim 1, wherein said 1-(4-fluoro-5-isoquinolinesulfonyl)-2-methyl-1,4-homopiperazine is administered to the subject suffering from physical injury to corneal endothelium or having progressive corneal endothelial dystrophy in an effective amount to prevent corneal edema.

* * * * *